United States Patent [19]

Lafferty

[11] 4,211,846

[45] Jul. 8, 1980

[54] PROCESSES FOR THE MANUFACTURE OF D(-)-3-HYDROXYBUTYRIC ACID AND D(-)-3-HYDROXYBUTYRIC ACID PRODUCING MUTANTS

[75] Inventor: Robert M. Lafferty, Graz, Austria

[73] Assignee: Agroferm AG, Chur, Switzerland

[21] Appl. No.: 821,858

[22] Filed: Aug. 4, 1977

[30] Foreign Application Priority Data

Aug. 4, 1976 [CH] Switzerland .................. 9957/76
Aug. 5, 1976 [CH] Switzerland .................. 10010/76

[51] Int. Cl.$^2$ .................................. C12D 13/02
[52] U.S. Cl. .......................... 435/141; 435/146; 435/172; 435/831; 435/829; 435/837; 435/822
[58] Field of Search .............. 195/28 R, 47, 49, 79, 195/96

[56] References Cited

U.S. PATENT DOCUMENTS

3,036,959  5/1962  Baptist .................. 195/47
3,044,942  7/1962  Baptist .................. 195/47

OTHER PUBLICATIONS

Harda et al., "Utilization of Alcohols by *Hnnsenula miso*," *Agr. Biol. Chem.,* vol. 32, No. 9, (1968) pp. 1175–1180.

Yagi et al., "Studies on the Utilization of Petrochemicals by Microorganisms," *Agr. Biol. Chem.,* vol. 33, No. 11, (1969) pp. 1587–1593.

Kersters et al., "The Oxidation of Glycols by Acetic Acid Bacteria," *Biochem. Biophys. Acta,* vol. 71, (1963) pp. 311–331.

*Primary Examiner*—Thomas G. Wiseman
*Attorney, Agent, or Firm*—Sughrue, Rothwell, Mion, Zinn and Macpeak

[57] ABSTRACT

The invention relates to a process of manufacturing D(-)-3-hydroxybutyric acid by breeding microorganisms capable of producing said acid in a nutrient medium containing certain specific carbon source; bacterial strains especially suitable in carrying out the process; an application of the process for obtaining such microorganisms; and uses of thus produced acid.

7 Claims, No Drawings

PROCESSES FOR THE MANUFACTURE OF D(-)-3-HYDROXYBUTYRIC ACID AND D(-)-3-HYDROXYBUTYRIC ACID PRODUCING MUTANTS

The present invention relates to a microbiological method of manufacturing D(−)-3-hydroxybutyric acid, microorganisms for use in such a method and methods of obtaining such microorganisms.

In the present application optically active 3-hydroxybutyric acids are designated according to the following definitions. Naturally occurring 3-hydroxybutyric acid or D(−)-3-hydroxybutyric acid (also, D(−)-β-hydroxybutyric acid) has a specific rotation $[\alpha]_D^{25}$ of −24.5° at a concentration of 5 g per 100 ml of water while L(+)-3-hydroxybutyric acid which does not occur in nature has a specific rotation $[\alpha]_D^{10}$ of +24.3° at a concentration of 2.226 g per 100 ml of water.

The 3-hydroxybutyric acid concerned herein unless the context otherwise provides is exclusively the isomer which has a negative rotation on the sodium D line i.e. the naturally occurring isomer, which for the sake of simplicity is henceforth designated by the abbreviation β-HB.

Various methods have been disclosed for the manufacture of racemic DL-3-hydroxybutyric acid; see e.g. Deutsche Offenlegungsschrift 441 003 and Wislicenus, Ann. 149 (1869), 207. McKenzie and Harden have also succeeded in manufacturing optically active pure L(+)-3-hydroxybutyric acid from DL-3-hydroxybutyric acid using *Aspergillus niger* [J. Chem. Soc., 83 (1903), 430]. However neither of these two forms are generally present in nature.

D(−)-3-hydroxybutyric acid occurs in humans, animals, plants and microorganisms (i.e. bacteria, yeasts, fungus and algae) as an essential substance in fat metabolism [Edstrom et al., Acta Obstet. gynecol. Scand. 54 (1975), 347; Moore et al. Am,J. Physiol 230 (1976), 619]. Because of this natural occurrence and physiological function, the compound could deserve great significance in, among other things, parenteral nutrition and as a starting material in the manufacture of chemical compounds which are compatible with the human organism.

It is, however, surprisingly true that hitherto, in contrast to the racemic and dextrorotatory i.e. non-naturally occurring 3-hydroxybutyric acid, no technically feasible method has been described for the manufacture of D(−)-3-hydroxybutyric acid. In particular, no microorganism has previously been found capable of separating out the desired carboxylic acid.

Surprisingly we have now found that microorganisms can be obtained, which separate out high concentrations of D(−)-3-hydroxybutyric acid starting from extremely cheap carbon sources and which can be improved still further in this respect.

Microorganisms particularly suitable for starting with are those which are able to synthesise butyric acid or poly-(D-3-hydroxybutyric acid), such as e.g. members of the genera Azotobacteraceae, Bacillaceae, Pseudomonadaceae, Methanomonadaceae, Spirillaceae, Achromobacteraceae and Enterobacteraceae.

Thus, microorganisms known to accumulate poly-(D-3-hydroxybutyric acid), such as e.g. *Alcaligenes eutrophus* ATCC 23440, *Azotobacter chroococcum* DSM 281, *Bacillus megatherium* ATCC 32, *Zoogloea ramigera* ATCC 19623 and the methanol-utiliser *Mycoplana rubra* CBS 385.76 isolated from air, may be bred e.g. on fructose as the sole carbon source under submerged conditions in such a way that as little poly(D-3-hydroxybutyric acid) as possible is accumulated. Such conditions include small C/N ratios and/or high oxygen partial pressures in the nutrient medium. After removal of the carbon source the microorganisms are placed into a medium which contains racemic or D(−)-3-hydroxybutyric acid as the sole carbon source and an antibiotic which destroys active or growing cells. The surviving, resting or non-growing, cells which do not form the enzyme 3-hydroxybutyric acid dehydrogenase (=EC 1.1.1.30; see E. T. Barman, Enzyme Handbook, Springer-Verlag, Berlin 1969) and thus cannot metabolise β-HB, are isolated and tested for their capacity to form β-HB. For this purpose, the concentration of β-HB is determined quantitatively in aliquots of the culture medium containing the microorganisms according to the enzymatic method of Williamson & Mellanby (Methods of Enzymatic Analysis, Verlag Chemie GmbH, Weinheim and Academic Press, Inc., New York 1974, Page 1883). The microorganisms capable of synthesising and separating out β-HB are selected and treated with mutagenic agents, e.g. with ultra-violet light, $NaNO_2$ or nitro-nitrosomethyl guanidine (see e.g. R. C. Clowes and W. Hayes, Experiments in Microbial Genetics, Blackwell Scientific Publications, Oxford and Edinburgh 1968). From the mutants thus produced may be selected those which produce, per unit volume of the culture medium, even higher concentrations of β-HB than the original strain.

In order to still further increase the capacity to produce D(−)-3-hydroxybutyric acid in the strains thus selected, they can be further mutated and of the resultant mutants, those may desirably be selected which reveal not only missing or impaired D(−)-3-hydroxybutyric acid dehydrogenase activity, but also missing or impaired activity of one or more enzymes of the tricarboxylic acid cycle (see Barman, loc. cit.).

On the other hand, microorganisms which do not accumulate poly-(D-3-hydroxybutyric acid) but form butyric acid, such as, for example, the Clostridium types, e.g. *Clostridium butyricum* ATCC 19398 may also be treated in a similar way, i.e. those organisms are selected which do not form any 3-hydroxybutyric acid dehydrogenase and, as a result, cannot metabolise β-HB. Thus, such strains may be bred on agar plates as scattered colonies. After growth has taken place, the agar surfaces may be spread with a mixture of 3-hydroxybutyric acid dehydrogenase, nicotine-adenine-dinucleotide in oxidised form (NAD) and a redox indicator consisting of methylene blue or triphenyltetrazolum chloride. A search may then be made for colonies which cause colour change of the redox indicator. These may be isolated and tested for their capacity to produce β-HB. Strains producing β-HB may be subjected to the mutation process mentioned above, in order to obtain derivatives with increased β-HB productivity.

According to the present invention, therefore, microorganisms may be selected which convert the maximum proportion of the carbon source into D(−)-3-hydroxybutyric acid in as short a time as possible by a method which comprises subjecting a microorganism capable of separating out butyric acid or D(−)-3-hydroxybutyric acid or of accumulating poly-(D-3-hydroxybutyric acid) to the action of mutagenic agents; selecting from the mutants thus obtained those which cannot metabolise D(—)-3-hydroxybutyric acid; and further selecting from the thus-selected mutants those which, optionally after further treatment with mutagenic agents, produce more D(—)-3-hydroxybutyric acid than the original microorganism when grown on a specific carbon source and under conditions mentioned below.

The microorganisms producing β-HB are advantageously accustomed by known methods to grow in high concentrations of specific carbon sources, i.e. carbon dioxide, assimilable carbohydrates, including e.g. glucose, fructose, saccharose, lactose, molasses and whey, assimilable alcohols, including e.g. methanol, ethanol and glycerin, and spent lyes from caprolactam synthesis, and thereby to produce β-HB. There can be added as a nitrogen source ammonium ions, and the usual trace elements as well. The derivatives of *Alcaligenes eutrophus* ATCC 23440 can, in addition to organic carbon sources such as those mentioned above, also metabolise carbon dioxide, if the atmosphere simultaneously contains molecular hydrogen and oxygen, in order to produce β-HB.

Preferred selected microorganisms thus obtained include mutants separating out D(—)-3-hydroxybutyric acid derived from *Alcaligenes eutrophus* ATCC 23440, e.g. the mutant CBS 381.76; from *Azotobacter chroococcum* DSM 281, e.g. the mutant CBS 383.76; from *Bacillus megatherium* ATCC 32, e.g. the mutant CBS 382.76; from *Zoogloea ramigera* ATCC 19623, e.g. the mutant CBS 384.76; from *Clostridium butyricum* ATCC 19398, e.g. the mutant CBS 380.76; and from *Mycoplana rubra* CBS 385.76 and mutants thereof. The above-mentioned strains are filed at the American Type Culture Collection (ATCC) 12301 Parklawn Drive, Rockville (Maryland, U.S.A.): Centraal Bureau voor Schimmelcultures (CBS), Oosterstraat 1, Baarn (Netherlands); and Deutsche Sammlung fur Mikroorganismen (DSM), Munich (BRD).

The microorganisms mentioned above, of course, can still further be improved in respect of their productivity by applying thereon the beforesaid methods.

To ensure that high yields are obtained in the large-scale manufacture of D(—)-3-hydroxybutyric acid, microorganisms are suitable which can produce at least 100 mg of the acid per liter of nutrient medium when bred under the conditions specified below and for a breeding period of 30 hours. It is, however, more preferred to use microorganisms whose production of β-HB is at least 200 mg/liter of nutrient medium for 30 hours under the same breeding conditions. Particularly preferred are microorganisms with a β-HB production (for 30 hours) of at least 500 mg/liter or even at least 1 g/liter of nutrient solution.

The carbon source content in the nutrient solution is advantageously approximately 2-25% glucose, fructose, saccharose, lactose, molasses or whey, calculated as pure carbohydrate, approximately 1-10% methanol, ethanol or glycerin or approximately 1-10% spent lye from caprolactam synthesis, calculated as the total amount of carboxylic acid contained therein.

Although all the microorganisms obtained according to the method of the present invention are capable of producing β-HB on solid nutrient media, liquid media are preferred for practical reasons. The microorganisms may be cultured according to conventional techniques as is well known in the art. Thus aqueous nutrient solutions having the carbon source concentration mentioned above and with an assimilable nitrogen source and the necessary trace elements may be prepared in known manner. The sterile nutrient media may, for example, be innoculated with 0.1-10% by volume of a preliminary culture and then incubated for 8-72 hours at approximately 25°-40° C. either in stationary culture or with exclusion of air for anaerobic microorganisms, e.g. the Clostridium types, or with stirring or shaking and optionally with a supply of air or a mixture of carbon dioxide, hydrogen and oxygen (or air) for aerobic microorganisms. To obtain as high a yield as possible of the desired D(—)-3-hydroxybutyric acid, the pH value of the inocculated solution is preferably maintained at 4-8 by the addition of a sterile alkali solution. During the growth of the culture, additional carbon source material may be added continuously, if desired, in order to maintain a constant concentration and achieve maximum production of β-HB.

Hence, the process according to the invention comprises breeding a microorganism, which produces D(—)-3-hydroxybutyric acid, at a temperature of approximately 25°-40° C. and a pH value of 4-8 in an aqueous nutrient medium which contains as carbon source carbon dioxide, an assimilable carbohydrate from the group glucose, fructose, saccharose, lactose, molasses and whey, an assimilable alcohol from the group methanol, ethanol and glycerin or the spent lye from caprolactam synthesis, together with an assimilable nitrogen source and trace elements, and isolating the D(—)-3-hydroxybutyric acid formed from the culture liquor by known methods.

After completion of fermentation, i.e. when the maximum concentration of β-HB is reached, the β-HB may, for example, be extracted by means of ion exchange resins optionally after separation of the culture mass from the fermented solution or, after acidification of the fermented solution to approximately pH 1.5-2.5, by means of solvents not miscible with water, such as e.g. ether, chloroform or other chlorinated hydrocarbons, ethyl acetate or other esters, isopropanol, butanol and other alcohols. β-HB can be precipitated from the organic solutions as a metal salt, e.g. the lithium, potassium, sodium, calcium, barium, nickel or zinc salt, or may be transformed into a concentrated aqueous solution.

D(—)-3-hydroxybutyric acid can be used especially in parenteral nutrition as it can replace in part or in full the fatty constituents used hitherto with regard to calorie supply, since it is substantially equivalent to the fats in this respect. In addition, however, it has the advantage that it is immediately available for intermediate metabolism, as compared with fats, which require either initial saponification and repeated β-oxidation.

As is also known odoriferous and aromatic substances occurring in fruit and plants consist partly of lower alkyl esters of D(—)-3-hydroxybutyric acid. Their synthetic manufacture, has, however, suffered hitherto from the impossibility of manufacturing D(—)-3-hydroxybutyric acid in a pure state by a technically feasible and economically productive method. In particular, no microorganisms have been known hitherto which separate out the desired carboxylic acid.

The method according to the invention, however, enables substantially pure D(—)-3-hydroxbutyric acid to be manufactured with a high yield from extremely cheap carbon sources and thus leads to the possibility of synthesising such optically active esters.

Thus the D(—)-3-hydroxybutyric acid manufactured according to the invention may be esterified with an optionally substituted lower alkanol according to known methods. For example, esterification may, for example, be carried out by treatment of the carboxylic acid with an excess of alkanol, particularly a $C_{1-5}$ alkanol, in the presence of a strong mineral acid, e.g. sulphuric acid.

The esters thus obtained have the same configuration as the corresponding odoriferous and aromatic substances occuring in fruit and plants. In contrast with the aromatic fruit substances manufactured hitherto using racemic DL-3-hydroxybutyric acid, the esters of D(—)-3-hydroxybutyric acid have the "natural" configuration which means that they are toxicologically harmless and, on a weight basis, have a significantly increased olfactory and organoleptic activity. Esters manufactured in this way may be used as odoriferous substances and aromatic substances in, for example, foodstuffs and perfumery.

The following examples illustrate the invention.

EXAMPLE 1

A nutrient solution is first prepared which contains 0.9% $Na_2HPO_4.12\ H_2O$, 0.15% $KH_2PO_4$, 0.1% $NH_4Cl$, 0.04% $MgSO_4.7\ H_2O$, 0.0195% iron (II)-$NH_4$-citrate .6 $H_2O$, 0.00133% $CaCl_2$ and, per liter of solution, 1 ml of a trace element solution containing 0.01% $ZnSO_4.7\ H_2O$, 0.003% $MnCl_2.4\ H_2O$, 0.03% boric acid, 0.02% $CoCl_2.6\ H_2O$, 0.001% $CuCl_2.2\ H_2O$, 0.002% $NiCl_2.6\ H_2O$ and 0.003% $Na_2MoO_4.2\ H_2O$. In 250 ml Erlenmeyer flasks, shaken or stationary cultures are bred, each with 30 ml of nutrient solution, at 30° C. for 16-24 hours. 20 ml of sterile-filtered fructose solution containing 10 g of fructose are added per 980 ml to the solution sterilised at 121° C. for 20 minutes. Inoculation is carried out by means of a loop from a 24-hour slant agar culture.

The shaken culture is sedimented on a centrifuge and the culture mass is washed with water and then suspended in approximately 4 ml of physiological saline solution. After approximately 1 hour 4 ml 0.6 N sodium acetate buffer of pH 4.6 and 4 ml of a 0.05 N sodium nitrite solution are optionally added to produce mutation and the culture is incubated for a few minutes. After washing, the culture mass of each microorganism (see following table) is distributed between 10 250 ml Erlenmeyer flasks to which are added the above medium except that it contains 2% DL-3-hydroxybutyric acid (or 1% D(—)-3-hydroxybutyric acid) instead of the fructose. After clouding has visibly started to increase in the flasks, each flask has added to it, depending on the organism, 1 ml of a sterile-filtered solution of 2-1000 μg/K-Penicillin G, 1 ml of a sterile-filtered solution of 30-1000 μg/ml Bacitracin, 1 ml of a sterile-filtered solution of 10-2000 μg phosphonomycin/ml, 5-1000 μg vancomycin/ml or mixtures of these and/or other antibiotics, such as e.g. colistin sulphate, which influence formation of the cellular wall or division of the microbes. After varying incubation periods, i.e. after 1-16 hours, the antibiotics are washed out or destroyed with penicillinase. After further washing of the culture mass the surviving microorganisms are inoculated into flasks containg a fructose medium and are incubated.

After 16-36 hours a series of dilutions are made from the cultures in each flask and from the dilutions, containing approximately 50-1000 organisms per ml, 0.1 ml are smeared on agar plates to obtain individual scattered colonies. The agar contains, as the sole carbon source, 2% sodium DL-3-hydroxybutyrate and 0.008% fructose. After approximately 48 hours a large number of small colonies of varying appearance of approximately ¼-1 mm diameter and colonies of normal size have formed. From each of the small colonies inocula are transferred by means of sterile dental slivers of wood, some onto a spot on an agar plate where sodium (DL)-3-hydroxybutyrate is the sole carbon source and others onto spots on an agar plate where fructose or glycerin is the sole carbon source. The desired strains, which can no longer metabolise β-HB and which possibly produce β-HB are to be found among those spontaneously present or artificially produced mutant colonies which cannot grow or can grow only poorly on 3-hydroxybutyric acid due to the absence or impairment of D(—)-3-hydroxybutyric acid dehydrogenase, but thrive well on an assimilable carbohydrate such as e.g. fructose or glycerin. The absence or impairment of D(—)-3-hydroxybutyric acid dehydrogenase activity is a prerequisite for a practically useable method of producing D(—)-3-hydroxybutyric acid.

These strains are over-inoculated on milky-cloudy lime agar prepared as follows: a solidified agar layer approximately 5 mm thick containing the nutrient solution mentioned in the introduction, provided with a suitable carbon source, is covered with a layer of the same sterile nutrient solution, which contains additionally 0.1% of pure, precipitated $CaCO_3$ in such a way that an upper layer approximately 1-2 mm thick arises. Colonies whose peripheral agar area lost its milky cloudiness and which were therefore surrounded by a transparent areola were found to produce acids.

Shaken cultures were made of these colonies in suitable submerged media in order to test their capacity to produce β-HB by the enzyme method of Williamson & Mellanby (loc. cit., see above). Good acid producers were inoculated by means of a loop from a slant agar culture into 500 ml Erlenmeyer flasks each containing 100 ml of nutrient solution (see above), each with 5 g/l of the appropriate carbon source (see Table) and the flasks were then incubated on a rotary shaker at 135 rpm and 30° C. After 30-52 hours samples were taken and analysed. The results are set out in following Table.

| | | Production of β-HB-producing microorganisms | | | | |
|---|---|---|---|---|---|---|
| | | 10,000 strains per type were analysed for acid-forming capacity | | | | |
| | | Number of βHB producing strains | | | Strains with maximum β-HB production | |
| Micro-organisms | Antibiotic treatment with | up to 1 mg/L | up to 10 mg/L | up to 95 mg/L | in mg/L | Designation of best strain | Carbon Source |
| Alcaligenes eutrophus ATCC 23440 and mutants thereof | — Penicillin/ Bacitracin | 0* ca.800 | — 6 | — 1 | — 54 | — GA-3 (CBS 381.76) | Fructose |

-continued

Production of β-HB-producing microorganisms
10,000 strains per type were analysed for acid-forming capacity

| Micro-organisms | Antibiotic treatment with | Number of βHB producing strains | | | | Strains with maximum β-HB production | Carbon Source |
|---|---|---|---|---|---|---|---|
| | | up to 1 mg/L | up to 10 mg/L | up to 95 mg/L | in mg/L | Designation of best strain | |
| *Bacillus megatherium* ATCC 32 | — | 0* | — | — | — | — | |
| and mutants thereof | Penicillin | ca.600 | 15 | 2 | 65 | GB-1 (CBS 382.76) | Saccharose |
| *Azotobacter chroococcum* DSM 281 | — | 0* | — | — | — | — | |
| and mutants thereof | Penicillin | ca.700 | 7 | 3 | 39 | GC-7 (CBS 383.76) | Saccharose |
| *Zoogloea ramigera* ATCC 19623 | — | 0* | — | — | — | — | |
| and mutants thereof | Phosphonomycin | ca.100 | 2 | 0 | 6 | GZ-1 (CBS 384.76) | Saccharose |
| *Clostridium butyricum* ATCC 19398 | — | 0* | — | — | — | — | |
| and mutants thereof | Bacitracin/Penicillin | ca.1'100 | 3 | 1 | 76 | GCl-2 (CBS 380.76) | Saccharose |
| *Mycoplana rubra* | — | 0* | — | — | — | — | |
| and mutants thereof | D-Cycloserine | ca.300 | 21 | 0 | 8 | GM-1 (CBS 385.76) | Glycerin or Methanol |

*Detectable neither in plate test nor enzymatically.

In a similar way, it was possible to obtain mutants which separate out β-HB in isolatable quantities by the application of other mutagenic agents, such as e.g. alkylating substances or radiation with e.g. ultra-violet light, or by isolating random spontaneous mutants.

In tests using *Clostridium butyricum*, the procedure is carried out in a similar way but under strict anaerobic conditions according to A. J. Schocher ["A Contribution to the Knowledge of Growth and Fermentation Physiology in Saccharolytic Clostrides", Dissertation, Laboratory for Microbiology, technische Hochschule Delft (Netherlands), 1959].

EXAMPLE 2

The β-HB producers GA-3 and GB-1 are subjected to the mutant selection process described in Example 1 and smeared onto agar plates in a similar way. After growth has finished, the colonies are applied by means of velvet stamps onto lime agar plates or fresh agar plates containing quantities of sterile bromocresol green or bromocresol purple as a pH indicator such that the agar is coloured either blue or purple. After short incubation periods, i.e. after only 5–6 hours, colour change of the pH indicator can be established, as a result of which colonies may be located which grow quickly and form a lot of acid. By means of this technique such colonies are selected and bred under submerged conditions in order to find their β-HB productivity. Most mutants of the β-HB producers used produce less β-HB or sometimes even no β-HB at all. However, among the many mutants obtained by mutation a few are perceived which produce more β-HB than the original strain. Such mutants are subjected to a new mutation/selection cycle in order to detect the strains which can produce even higher concentrations of β-HB.

The selected strains were bred at 30° C. in shaken culture tubes (test tubes 16 mm in diameter) containing 5 ml of sterile nutrient medium, which are fastened at an angle of 45° to a plate oscillating horizontally at 135 rpm. In this way it was possible to obtain from the strain *Alcaligenes eutrophus* GA-3 (CBS 381.76) a culture which produced 95 mg β-HB/L on 5% fructose in 51 hours. A new mutation/selection process supplied a culture which produced approximately 400 mg β-HB/l under the same conditions.

It was possible to derive in a similar way from the strain *Bacillus megatherium* GB-1 (CBS 382.76) a shaken culture which formed 145 mg β-HB/L on saccharose within 54 hours. A new mutation/selection process supplied a shaken culture which produced more than 1 g β-HB/L under the same conditions.

The yields of β-HB could be increased still further by additional mutation/selection processes.

EXAMPLE 3

The mutant 31 N selected from *Bacillus megatherium* strain GB-1 was incubated in a 5-liter small fermenter (brand Biostat V, Braun-Melsungen) with 2.5 liters of the nutrient solution of Example 1, which contained, instead of fructose, 24 g of saccharose per liter and 100 mg peptone per liter. 100 ml of a culture in the same medium shaken overnight served as an inoculum. Air was blown through the small fermenter at 30° C. with approximately 0.5 volume/volume minute and agitated at 600 rpm. During breeding the pH was kept between 7.2 and 7.3 by the addition of 10% sodium hydroxide solution. After 30 hours the fermented solution contained 170 mg β-HB/liter. The product was absorbed from the supernatant fluid on Amberlite 410A in OH form and was eluted with 0.5 N sulphuric acid. The highly concentrated eluate was treated by the extraction process of P. A. Schaffer and W. M. Mariott [J. Biol. Chem., 16, 268 (1913)], as a result of which it was possible to isolate 330 mg of the calcium-zinc mixed salt of β-HB. After recrystallisation 3 times from ethanol/- water the result was a product whose solution (8.027 g per 100 ml H$_2$O) at a layer thickness of 20 cm gave a rotation of the Na D line of $-2.60°$, which corresponds to a $[\alpha]_D^{20}$ of $-16.2$ agreeing with the literature.

EXAMPLE 4

In a similar way to Example 3, a medium was used which contained glucose instead of saccharose. It was possible to isolate 350 mg calcium-zinc D(−)-3-hydroxybutyrate.

EXAMPLE 5

In a similar way to Example 3, a medium was used which contained, instead of saccharose, 50 g of beet molasses per liter with a saccharose content of 51%. The resultant fermented solution contained 160 mg β-HB/liter after an incubation of 31 hours.

In a similar way to that above, saccharose was used with the same success.

EXAMPLE 6

Under anaerobic conditions the mutant GCl-112 from *Clostridium butyricum* ATCC 19398 was incubated for 48 hours in a medium containing 4% saccharose, 0.3% $NH_4$ acetate, 0.178% $Na_2HPO_4.2H_2O$, 0.136% $KH_2PO_4$, 0.042% $MgSO_4.7\ H_2O$, 0.00025% $FeSO_4.7\ H_2O$, 0.0013% $MnCl_2.4\ H_2O$ and 1 μg (+)-Biotin per 1000 ml, after which the fermented medium had a concentration of 171 mg β-HB/liter.

EXAMPLE 7

To find microorganisms capable of utilising methanol, a 500 ml beaker was filled with approximately 100 ml of the nutrient solution of Example 1 except that it contained 1% methanol as the sole carbon source. After a few days the culture was cloudy and individual scattered colonies could be produced from it after appropriate dilutions with water on agar plates with the medium from Example 1. From the selected colonies, shaken cultures are bred in the glycerin medium mentioned above and are analysed according to Law and Slepecky [J. Bact., 82 (1961), 33] for poly-β-hydroxybutyric acid production. In this way, a rod-shaped microorganism is obtained which forms up to 50% by weight of its cellular mass of poly-β-hydroxybutyric acid and has been identified by the curator of the National Collection of Industrial Bacteria (Ministry of Agriculture, Fisheries and Food, Torry Research Station, Aberdeen, Scotland) as a *Mycoplana rubra* strain. The strain has been registered at the Centraal Bureau voor Schimmelcultures under the designation CBS 385.76 and named originally *Bacterium in editio Pl.* It was characterised as follows:

Morphology (GP Agar, consisting of 1% glycerin+1% peptone at pH 7.0 on agar, 6 days at 30° C.). Pleomorphous rods 0.8×1.5–5.0 μm, cells contain a high percentage of poly-β-hydroxybutyric acid.

Older submerged cultures, i.e. more than 7 days old, contain small quantities of cells with primary cellular branches which are detectable under a phase-contrast microscope.

Colony (GP Agar, 6 days at 30° C.).

Pink-coloured pigment, transparent, round, edged, convex, smooth and shining, diameter 0.5–1.0 mm. Pigmentation is intensified with increasing age. Very poor growth on blood agar base (OXOID CM 55).

Submerged growth (GP nutrient solution, consisting of 1% glycerin+1% peptone at pH 7.0, 6 days at 30° C.). rather weak growth, forms surface ring and membrane, slightly viscous sediment.

Temperature:
At 10° C., little or no growth
At 15° C., growth
At 30° C., growth
At 37° C., no growth
Gram Staining negative to variable
Mobility +
Kovacs' Oxidase +
Catalase +
Hugh and Leifson (Glucose) OF−

Peptone water carbohydrates: acid formation on glycerin. no acid formation on glucose, fructose, maltose, saccharose, lactose, starch or mannitol.

Indol production −
Methyl red −
Voges-Proskauer −
Koser's Citrate −
Tryptone Weak formation of $NH_4^+$ −
Nitrate reduction −
Urease (Christensen) +
Starch Weak hydrolysis
Gelatine Not hydrolysed
Casein Not hydrolysed
Haemolysis −

Antibiotic Sensitivity

Resistant to penicillin, chloramphenicol and polymyxin B; sensitive to streptomycin and tetracyclin.

Can utilise methanol but not methane as sole carbon source.

EXAMPLE 8

A procedure similar to that of Example 3 was carried out with the derivative GM-37 of the *Mycoplana rubra* strain (CBS 385.76) freshly isolated from air and utilising methanol, except that in the medium the saccharose was replaced by 2.5% methanol. After an incubation period of 48 hours at 30° C. the fermented solution contained 36 mg β-HB/liter.

EXAMPLE 9

The mutant H-7 selected from *A. eutrophus* strain GA-3 (CBS 381.76) was bred in a similar way to Example 3 in a small fermenter in the medium of Example 1, but without an organic carbon source and with aeration with 0.11 volume/volume.minute of a gas mixture containing 10% $CO_2$, 20% $O_2$ and 70% $H_2$ at 28° C. with agitation, the pH value being kept at 7.0 by the addition of 10% NaOH. After 51 hours the fermented solution contained 30 mg β-HB/liter.

EXAMPLE 10

A further method which was used successfully to detect and select strains with high β-HB productivity comprised analysing cells obtained according to Example 1 and 2 in a short experiment for their β-HB formation kinetics. For this purpose, the cellular mass of a shaken culture 30 hours old was centrifuged, washed with a physiological common salt solution and suspended in fresh medium with a suitable carbon source and incubated e.g. in a Warburg respiratory apparatus. Cellular suspensions with higher capacity to form β-HB were distinguished by high $O_2$ absorption. The β-HB formation kinetics of such suspensions were determined by enzymatic analysis. Strains with substantially increased β-HB formation capacity in relation to the parent strain were plated out in order to obtain pure clones for the production of β-HB.

In this way, it was possible to find from *B. megatherium* GB-1 sub-strains which secreted e.g. on molasses per minute and gramm of cellular dry mass 1.5 mg β-HB (e.g. the mutant 24 N). In the same test set-up it was possible to establish, for example, that the strain *B. megatherium* reaches its maximum production rate of β-HB at pH 5.

EXAMPLE 11

Further observation showed that mutants whose synthesis capacity in the citric acid cycle is disturbed form considerably higher quantities of β-HB than their normal parent strains. For example, the *B. megatherium* strain 24 N was treated with the deadening method using penicillin described in Example 1, having been previously treated with a mutagenic agent. Those mutants were selected and enriched which could not grow or could only grow poorly without additions of citric acid, succinic acid and glutamic acid. In this way, 4 mutant colonies were found which did not grow to an optimum degree without the addition to the medium of small quantities of the above-mentioned organic acids. One of these 4 mutants produced in a shaken culture using the medium of Example 1, with 1% saccharose and additional 0.05% meat extract, 0.01% citric acid, 0.01% succinic acid and 0.01% glutamic acid, in a 15-hour incubation, 11.75 times the quantity of β-HB that its parent strain 24 N produced under the same conditions.

EXAMPLE 12

Two groups of six young rabbits, each of approximately 500 g average body weight, were fed exclusively by means of a *Vena cava* catheter (*Vena jugularis julema*) at an infusion rate of 6 ml/hour. The animals of the control group received a solution containing 695 kcal per liter, i.e. approximately 17 g of peptides plus amino acids (=11 cal %), approximately 97 g carbohydrates (=48 cal %) and approximately 34 g fat (=41 cal %) and mineral substances and vitamins. In the test group 20% by weight of the fats were replaced by sodium D(−)-3-hydroxybutyrate. After 10 days the average increase in weight of the animals of both groups was identical. An increase in the proportion of D(−)-3-hydroxybutyric acid to 30% by weight of the fat constituents of the infusion solution led after 5 days to the same increase in weight as in the control group.

EXAMPLE 13

1 g of the D(−)-3-hydroxybutyric acid is dissolved in 100 ml of ethanol and approximately 1 ml of concentrated $H_2SO_4$ is added to the resultant solution. The reaction mixture is stirred for 3 hours at room temperature with a magnetic stirrer and then diluted with 1 volume of water and treated with a quantity of diethyl ether so as to result in a 2-phase mixture. The organic phase is thoroughly washed with water and the ether is then distilled off under vacuum. The residue contains ethyl D(−)-3-hydroxybutyrate with a raspberry-like aroma; boiling point 184°–185° C./755 mm, $[\alpha]_D^{25} = -10.5°$ (not completely pure optically). On a weight basis the ester has considerably stronger aromatic properties than the ethyl ester of DL-3-hydroxybutyric acid obtainable commercially.

EXAMPLE 14

The extract of the fermented solution of Example 2, using *Bacillus megatherium* ATCC 32 strain CBS 382.76, is treated with an equal volume of ethanol, approximately 25 g $Na_2SO_4$ and 3 ml concentrated $H_2SO_4$ and stirred for 5 hours. The reaction mixture is then washed with a lot of water and the organic phase is then concentrated under vacuum. The same ethyl ester is obtained with the same properties as described in Example 13.

EXAMPLE 15

The procedure is conducted in a similar way to that of Example 14, but methanol is used instead of ethanol. From the evaporation residue methyl D(−)-3-hydroxybutyrate is obtained which has the aroma of fruit, boiling point 67°–68.5° C. $[\alpha]_D^{20} = -20.9°$ (without solvent).

EXAMPLE 16

The procedure is carried out in a similar way to that of Example 14 using the fermented solution of Example 6 instead of Example 2 and propyl alcohol instead of ethanol. The result is similar to that of Example 15.

EXAMPLE 17

The procedure is carried out in a similar way to that of Example 14 using the fermented solution of Example 7 instead of Example 2 and butyl alcohol instead of ethanol. The result is similar to that of Example 15.

EXAMPLE 18

The procedure is conducted in a similar way to that of Example 14 using the fermented solution of Example 9 instead of Example 2 and amyl alcohol instead of ethanol. The result is similar to that of Example 15.

What is claimed is:

1. A process for producing D(−)-3-hydroxybutyric acid which comprises cultivating a mutant microorganism on an aqueous nutrient medium containing trace elements, an assimilable nitrogen source and a carbon source selected from the group consisting of carbon dioxide, glucose, fructose, saccharose, lactose, molasses, whey, methanol, ethanol, glycerin and spent lye from caprolactam synthesis under conditions and for a time sufficient to produce said D(−)-3-hydroxybutyric acid and isolating said D(−)-3-hydroxybutyric acid from the medium, wherein said mutant microorganism does not form 3-hydroxybutyric acid dehydrogenase and produces at least 100 mg/liter of D(−)-3-hydroxybutyric acid when cultivated on said nutrient medium for 30 hours at a temperature between 25° and 40° C. and at a pH value between 4 and 8.

2. A process according to claim 1 wherein the microorganism mutant used is the D(−)-3-hydroxy-butyric acid-producing mutant derived from *Alcaligenes eutrophus* ATCC 23440, *Azotobacter chroococcum* DSM 281, *Bacillus megatherium* ATCC 32, *Zoogloea ramigera* ATCC 19623, *Clostridium butyricum* ATCC 19398 and *Mycoplana rubra* CBS 385.76.

3. A process according to claim 1, wherein when the carbon source is selected from the group consisting of glucose, fructose, saccharose, lactose, molasses or whey, the concentration of the carbon source is 2–25% weight/volume, when the carbon source is selected from the group consisting of methanol, ethanol or glycerin the concentration of the carbon source is 1–10% weight/volume, and when the carbon source is spent lye from caprolactam synthesis the concentration of the carbon source is 1–10% weight/volume, calculated as the total quantity of carboxylic acids contained therein.

4. A process according to claim 1 wherein cultivation is effected under aerobic conditions with aerobes and under anaerobic conditions with anaerobes.

5. The process of claim 1, wherein said microorganism mutant is obtained by exposing a parent microorganism which yields said microorganism mutant to a mutagenic agent selected from the group consisting of ultraviolet light, nitro-nitrosomethyl guanidine, sodium nitrite and alkylating substances.

6. A process for producing a microorganism mutant capable of converting into D(−)-3-hydroxybutyric acid a maximum amount of a carbon source selected from the group consisting of carbon dioxide, glucose, fructose, saccharose, lactose, molasses, whey, methanol, ethanol, glycerin and spent lye from caprolactam synthesis within a minimum space of time, which comprises (1) subjecting a microorganism capable of excreting butyric acid or D(−)-3-hydroxybutyric acid, or of accumulating poly(D-3-hydroxybutyric acid), and which does not form the enzyme 3-hydroxybutyric acid dehydrogenase, to the action of a mutagenic agent, (2) selecting from the mutants thus obtained those which cannot metabolise D(−)-3-hydroxybutyric acid and (3) selecting from the thus obtained mutants those which are capable of producing at least 100 mg of D(−)-3-hydroxybutyric acid per liter of the nutrient medium within 30 hours when cultivated at a temperature of approximately 25°–40° C. and a pH value of approximately 4–8 in an aqueous nutrient medium which contains a carbon source as specified above.

7. The process of claim 6, wherein said mutagenic agent is selected from the group consisting of ultraviolet light, nitro-nitrosomethyl guanidine, sodium nitrite and alkylating substances.

* * * * *